(12) United States Patent
Strader et al.

(10) Patent No.: US 10,695,423 B2
(45) Date of Patent: *Jun. 30, 2020

(54) PREDILUTION SETS FOR DISTRIBUTING ANTIGENS

(71) Applicant: ROCA MEDICAL LTD., London (GB)

(72) Inventors: James Strader, Austin, TX (US); Jovan Pulitzer, Frisco, TX (US)

(73) Assignee: ROCA Medical Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/654,887

(22) Filed: Oct. 16, 2019

(65) Prior Publication Data

US 2020/0038507 A1 Feb. 6, 2020

Related U.S. Application Data

(63) Continuation of application No. 16/531,576, filed on Aug. 5, 2019, which is a continuation of application
(Continued)

(51) Int. Cl.
*A61K 39/35* (2006.01)
*A61K 39/00* (2006.01)

(52) U.S. Cl.
CPC .............. *A61K 39/35* (2013.01); *A61K 39/00* (2013.01)

(58) Field of Classification Search
CPC .. A61K 39/35; A61K 39/385; A61B 10/0096; A61F 17/00; B65D 79/02;
(Continued)

(56) References Cited

U.S. PATENT DOCUMENTS

| D247,822 S | 5/1978 | Hein et al. |
| 4,195,734 A | 4/1980 | Boner et al. |

(Continued)

OTHER PUBLICATIONS

Baumann L.S. et al., "Lip Silicone Granulomatous Foreign Body Reaction Treaded with Aldara (Imiquimod 5%)", Dermatologic Surgery 20030401 US, vol. 29, No. 4, Apr. 1, 2003 (Apr. 1, 2003), pp. 429-432, XP002745005, ISSN: 1076-0512, p. 429, left-hand column, paragraph middle. Apr. 1, 2003.
(Continued)

*Primary Examiner* — Rafael A Ortiz
(74) *Attorney, Agent, or Firm* — Gregory M. Howison

(57) ABSTRACT

A method for delivering allergens to a pharmacist in a pre-diluted kit form, comprising providing a bulk container of base concentrate antigen containing at least one antigen at a predetermined concentrated level, creating a sequential and more diluted sequence of antigens, providing a plurality of end-use sealable containers that can receive a finite end amount of diluted antigens, dispensing from each of sequential bulk containers a finite end amount of diluted antigens into one of the plurality of end-use sealable containers, wherein the end-use seal containers filled from each of the sequential bulk containers comprises a group of end-use sealable containers associated with each of the sequential bulk containers, sealing each of the end-use containers after diluted antigens are disposed therein, and disposing a select number of the sealed end-use sealable containers from each of the groups of end-use sealable containers into a container comprising a kit.

7 Claims, 15 Drawing Sheets

Related U.S. Application Data

No. 15/183,719, filed on Jun. 15, 2016, now Pat. No. 10,369,215, which is a continuation-in-part of application No. 15/171,920, filed on Jun. 2, 2016.

(60) Provisional application No. 62/169,785, filed on Jun. 2, 2015, provisional application No. 62/169,787, filed on Jun. 2, 2015, provisional application No. 62/180,003, filed on Jun. 15, 2015, provisional application No. 62/176,000, filed on Jun. 15, 2015, provisional application No. 62/349,626, filed on Jun. 13, 2016.

(58) Field of Classification Search
CPC ........ B65D 77/00; B65D 69/00; B65D 71/00; A61J 1/16; G01N 2001/005
USPC ............. 206/569, 570, 223, 459.1, 363, 364
See application file for complete search history.

(56) References Cited

U.S. PATENT DOCUMENTS

| | | | |
|---|---|---|---|
| 4,292,979 A | 10/1981 | Inglefield, Jr. et al. | |
| 4,657,138 A | 4/1987 | Watson | |
| 4,666,441 A | 5/1987 | Andriola et al. | |
| 4,976,351 A | 12/1990 | Mangini et al. | |
| 5,647,371 A | 7/1997 | White et al. | |
| 6,340,455 B1 | 1/2002 | Blomlof et al. | |
| 6,488,937 B1 | 12/2002 | Smits | |
| 7,297,136 B2 | 11/2007 | Wyrick | |
| 7,806,265 B2 | 10/2010 | Timm | |
| 8,328,082 B1 | 12/2012 | Bochenko et al. | |
| 8,491,909 B2 | 7/2013 | Esch | |
| 9,539,318 B2 | 1/2017 | Dupont et al. | |
| 10,149,904 B2 | 12/2018 | Nadeau | |
| 2002/0019358 A1* | 2/2002 | Manthorpe | A61K 48/00 514/44 R |
| 2002/0061315 A1 | 5/2002 | Kundig et al. | |
| 2003/0042170 A1* | 3/2003 | Bolanos | A61B 10/0096 206/570 |
| 2003/0065537 A1 | 4/2003 | Evans | |
| 2003/0082212 A1 | 5/2003 | Smits | |
| 2004/0106146 A1 | 6/2004 | Palosuo et al. | |
| 2004/0185055 A1 | 9/2004 | Glenn et al. | |
| 2004/0256026 A1 | 12/2004 | Py | |
| 2005/0096785 A1 | 5/2005 | Moncrief et al. | |
| 2005/0101905 A1 | 5/2005 | Merry | |
| 2005/0119622 A1 | 6/2005 | Temple | |
| 2005/0175638 A1 | 8/2005 | Esch | |
| 2006/0020514 A1 | 1/2006 | Yered | |
| 2006/0212318 A1 | 9/2006 | Dooley et al. | |
| 2007/0084742 A1 | 4/2007 | Miller et al. | |
| 2007/0142786 A1 | 6/2007 | Lampropoulos et al. | |
| 2009/0143745 A1 | 6/2009 | Langan et al. | |
| 2009/0169602 A1 | 7/2009 | Senti et al. | |
| 2009/0255843 A1 | 10/2009 | Krakowski | |
| 2011/0018226 A1 | 1/2011 | Jessie, Jr. | |
| 2011/0118226 A1 | 5/2011 | Masini-Eteve | |
| 2011/0142867 A1 | 6/2011 | Larche et al. | |
| 2011/0233079 A1 | 9/2011 | Macinnes et al. | |
| 2011/0236416 A1 | 9/2011 | Audonnet et al. | |
| 2011/0282690 A1 | 11/2011 | Patel et al. | |
| 2012/0000592 A1 | 1/2012 | Mase et al. | |
| 2012/0076825 A1 | 3/2012 | Webster et al. | |
| 2012/0185276 A1 | 7/2012 | Shah | |
| 2012/0325721 A1* | 12/2012 | Plante | A61B 10/0051 206/577 |
| 2013/0102772 A1 | 4/2013 | Eshima et al. | |
| 2013/0161351 A1 | 6/2013 | Eini et al. | |
| 2013/0313156 A1 | 11/2013 | Duncan | |
| 2014/0010845 A1 | 1/2014 | Brimnes et al. | |
| 2014/0276196 A1 | 9/2014 | Niederauer et al. | |
| 2014/0316796 A1 | 10/2014 | Cox | |
| 2014/0346068 A1 | 11/2014 | Omura et al. | |
| 2015/0231033 A1* | 8/2015 | Agren | B65D 25/108 206/568 |
| 2015/0238263 A1* | 8/2015 | Nicoletti | A61J 1/16 211/126.12 |
| 2015/0338388 A1* | 11/2015 | Pepe | A61B 5/150702 141/65 |
| 2015/0342514 A1 | 12/2015 | Easton | |
| 2016/0030368 A1 | 2/2016 | Atkins, Jr. et al. | |
| 2016/0136049 A1 | 5/2016 | Weinstein et al. | |
| 2016/0199257 A1 | 7/2016 | Husnu et al. | |
| 2016/0324955 A1 | 11/2016 | Benhamou et al. | |
| 2017/0333386 A1 | 11/2017 | Lila et al. | |

OTHER PUBLICATIONS

Cox et al., J. Allergy Clin. Immunol. 2011; 127(1 ):S1-S55 Jan. 1, 2011.

E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

El Maghraby et al. Eur. J. Pharma. Sci. 2008; 34:203-222 Apr. 18, 2008.

PCT: European Patent Office Searching Authority, International Search Report and Written Opinion of PCT/IB2015/001330 (related application), dated Oct. 5, 2015, 14 pgs. Oct. 5, 2015.

PCT: European Patent Office Searching Authority, International Search Report and Written Opinion of PCT/IB2016/001332 (related application), dated Nov. 24, 2016, 13 pgs. Nov. 24, 2016.

Prieto-Garcia Alicia et al: "Autoimmune Progesterone Dermatitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, p. 1121.e9, left-hand column p. 1121.e12, left-hand column, paragraph top Mar. 1, 2001.

* cited by examiner

| SINGLE ANTIGEN TABLE ||||||||| 
|---|---|---|---|---|---|---|---|---|
| NDC | ANTIGEN | DILUTION PROCEDURE | D1 (BASE) | D2 | D3 | D4 | D5 | D6 |
| XXX | CAT | STANDARD | X1 | X2 | X3 | X4 | X5 | X6 |
|  |  |  | Y1 | Y2 | Y3 | Y4 | Y5 | Y6 |
|  |  |  | Z1 | Z2 | Z3 | Z4 | Z5 | Z6 |
| ooo | ooo | ooo | ooo | ooo | ooo | ooo | ooo | ooo |
| YYY | DOG | STANDARD | X1 | X2 | X3 | X4 | X5 | X6 |
|  |  |  | Y1 | Y2 | Y3 | Y4 | Y5 | Y6 |
|  |  |  | Z1 | Z2 | Z3 | Z4 | Z5 | Z6 |
| ooo | ooo | ooo | ooo | ooo | ooo | ooo | ooo | ooo |

FIG. 12

| DILUTION PROCEDURE | D1 | D2 | D3 | D4 | D5 | D6 |
|---|---|---|---|---|---|---|
| S1 | Z1 | Z2 | Z3 | Z4 | Z5 | Z6 |
| S2 | Z1' | Z2' | Z3' | Z4' | Z5' | Z6' |
| S3 | Z1" | Z2" | Z3" | Z4" | Z5" | Z6" |

FIG. 12A

PREDILUTION SETS FOR DISTRIBUTING ANTIGENS

CROSS-REFERENCE TO RELATED APPLICATIONS

This application is a Continuation of U.S. application Ser. No. 16/531,576, filed Aug. 5, 2019, entitled PREDILUTION SETS FOR DISTRIBUTING ANTIGENS. U.S. application Ser. No. 16/531,576 is a Continuation of U.S. application Ser. No. 15/183,719, filed Jun. 15, 2016, issued as U.S. Pat. No. 10,369,215 on Aug. 6, 2019, and entitled PREDILUTION SETS FOR DISTRIBUTING ANTIGENS. U.S. application Ser. No. 15/183,719 is a Continuation-In-Part of U.S. application Ser. No. 15/171,920, filed on Jun. 2, 2016, entitled METHOD FOR MANAGING REIMBURSEMENTS FOR PREVIOUSLY NON DATABASE ALLERGENS. U.S. application Ser. No. 15/171,920 claims the benefit of U.S. Provisional Application No. 62/169,785, filed on Jun. 2, 2015, and entitled METHOD FOR MANAGING REIMBURSEMENTS FOR PREVIOUSLY NON DATABASE ALLERGENS, and of U.S. Provisional Application No. 62/169,787, filed on Jun. 2, 2015, entitled METHOD FOR REPURPOSING NDC CODES IN A PHARMACEUTICAL DATABASE FOR ALLERGENS. U.S. application Ser. No. 15/183,719 claims the benefit of U.S. Provisional Application No. 62/180,003, filed on Jun. 15, 2015, entitled USE OF AUTOINJECTOR FOR DISTRIBUTING ANTIGENS TO THE PUBLIC, and of U.S. Provisional Application No. 62/176,000, filed on Jun. 15, 2015, entitled PREDILUTION SETS FOR DISTRIBUTING ANTIGENS. U.S. application Ser. No. 15/183,719 also claims the benefit of U.S. Provisional Application No. 62/349,626, filed on Jun. 13, 2016, entitled METHOD AND APPARATUS FOR COMPLETING PRESCRIPTION FOR ALLERGEN COCKTAIL WITH PATCH. U.S. application Ser. Nos. 16/531,576, 15/183,719, 15/171,920 and U.S. Provisional Application Nos. 62/169,785, 62/169,787, 62/180,003, 62/176,000 and 62/349,626 are incorporated by reference herein in their entirety.

This application is related to co-pending U.S. patent application Ser. No. 15/183,721, filed on Jun. 15, 2016, and entitled USE OF AUTOINJECTOR FOR DISTRIBUTING ANTIGENS TO THE PUBLIC, which is incorporated by reference herein in its entirety.

TECHNICAL FIELD

That this application is generally related to the delivery of immunomodulators to a patient.

BACKGROUND

Immunotherapy (IT) is recognized as one of the most curative treatment for allergies. By exposing the immune system to slowly increasing concentrations of immunomodulators such as an allergen or antigen, it will eventually stabilize and regain control the portion that is hypersensitive to the allergen or antigen. In general, immunotherapy is the "treatment of disease by inducing, enhancing, or suppressing an immune response." Immunotherapies designed to elicit or amplify an immune response are classified as activation immunotherapies, while immunotherapies that reduce or suppress are classified as suppression immunotherapies. The active agents of immunotherapy are collectively called immunomodulators. They are a diverse array of recombinant, synthetic and natural preparations, often cytokines.

Immunotherapy involved in the treatment of allergies is a type of suppression immunotherapy, often termed desensitization or hypo-sensitization. This is compared with allergy treatments such as antihistamines or corticosteroids which treat only the symptoms of allergic disease. Immunotherapy is the only available treatment that can modify the natural course of the allergies, by reducing sensitivity to the immunomodulators such as antigens or allergens. An antigen and an allergen can both cause one's immune system to respond. An allergen is an antigen, but not all antigens are allergens. An antigen is any substance that is capable of causing one's immune system to produce antibodies. They are typically organic, or living, produced proteins. An allergen is any antigen that causes an allergic reaction. A non-allergen antigen could be a bacteria, virus, parasite, or fungus that causes an infection. This could also be something else that causes antibody immune system response, like toxins, chemicals, tissue cells involved in transplants or blood cells from a blood transfusion. An allergen is an environmentally produced substance that causes an allergic reaction, although the substance may not be harmful. Allergens cause no reactions in some individuals, while possibly causing a hypersensitive reaction in others. Common allergens include such things as pollen, plants, smoke, feathers, perfumes, dust mites, toxic mold, food, drugs, animal dander, and insect bites and stings.

The exact mechanisms of how IT works are not fully understood, but they involve shifting a patient's immune response from a predominantly "allergic" T-lymphocyte response to a "non-allergic" T-lymphocyte response.

Current accepted processes for performing allergy immunotherapy include injecting immunomodulator matter in the form of antigen material into patient subjects. This is referred to as subcutaneous immunotherapy (SCIT), requiring a patient to visit a doctor's office for weekly injections. It's is very expensive and time-consuming. A second technique, sublingual immunotherapy (SLIT), involves the application of allergy extracts (antigens), and allergens placed into a pill form and swallowed by the patient or disposed in "allergy drops" which are placed under the tongue for the allergens/antigens to be absorbed into the oral mucosa. Transdermal patches may have been used without much success and mostly were used for patch testing to see if a patient reacts to various chemicals or allergens.

Of the people who start traditional subcutaneous injected immunotherapy (SCIT), 90% fail to complete their therapy due to needle fatigue and not being able to see a doctor in their office once or more per week for several years. Further, doctors charge for every one of those visits. Further, doctors trained to give injections for allergy are concentrated in high population and upper middle class places. People in rural areas and people who do not live in upper middle class areas cannot get to an allergist for shots. Consider an inner city kid having to ride public transportation and pay a high copay just to get a high risk injection if an alternative therapy were available!

Allergies are also linked to depression and suicide and are among the top ten reasons for missed work and lost productivity. Lastly, allergies and asthma result in billions of dollars in lost productivity and healthcare costs among the 90% of allergy patients that either never get immunotherapy or fail immunotherapy delivered under its current administration methods.

Currently, allergens are not readily reimbursed when received from a pharmacist for the simple reason that the National Drug Code (NDC) code is not included in the database to which the pharmacist has access. Without an NDC code in the database, the pharmacist cannot access that information. By not being able to access information, the pharmacist cannot interface with a benefits provider for reimbursements nor can they have access to the Average Wholesale Price (AWP), which is the benchmark that has been used for many years for pricing and reimbursement of prescription drugs for both government and private payers. Initially, this AWP was intended to represent the average price that wholesalers used to sell medications to providers, such as physicians, pharmacies, and other customers. However, the AWP is not a true representation of actual market prices for either generic or brand drug products. AWP has often been compared to the "list price" or "sticker price", meaning it is an elevated drug price that is rarely what is actually paid. AWP is not a government-regulated figure, does not include buyer volume discounts or rebates often involved in prescription drug sales, and is subject to fraudulent manipulation by manufacturers or even wholesalers. As such, the AWP, while used throughout the industry, is a controversial pricing benchmark.

The AWP may be determined by several different methods. The drug manufacturer may report the AWP to the individual publisher of drug pricing data, such as Medi-Span. The AWP may also be calculated by the publisher based upon a mark-up specified by the manufacturer that is applied to the wholesale acquisition cost (WAC) or direct price (DIRP). The WAC is the manufacturer's list price of the drug when sold to the wholesaler, while the DIRP is the manufacturer's list price when sold to non-wholesalers. Typically a 20% mark-up is applied to the manufacturer-supplied WAC or DIRP, which results in the AWP figure.

The publishers then in turn sell these published AWPs to government, private insurance, and other buyers of prescription drugs, who use these data tables to determine reimbursement and retail prices. Because AWP is a component of the formulas used to determine reimbursement, elevated AWP numbers can drastically increase the dollar amount that government, private insurance programs, and consumers with coinsurance must pay.

Pharmacies typically buy drugs from a wholesaler and then sell them to the public. Many patients have coinsurance or copayments, where they only pay for a portion of their prescription cost. The insurance company then pays the rest of the cost (the reimbursement) to the pharmacy. Insurance companies include prescription benefit manager (PBM), health maintenance organization (HMO) or government programs, such as Medicaid or Medicare Part B or D. In addition, the pharmacy receives a dispensing fee for filling the prescription. Fees are, for example, set between $3 to $5 per prescription, but may vary by state.

Reimbursements are based on AWPs. However, pharmacies purchase drugs based on the WAC. The difference between the WAC (what the pharmacy actually paid for the drug) and the reimbursement from insurance (based on AWP) is known as the spread, and equates to the profit that the pharmacy receives. Market pricing on brand drugs tend to be about 16.6 percent less than the AWP.

However, the relation of AWP to generic pricing is not clear. Older generics tend to have a large spread between the AWP and WAC, which in turn gives a large spread, and higher profit margins for the pharmacy or other provider of the drug. Many payers, such as PBMS or HMOs, will determine a maximum allowable cost (MAC) pricing on generics to avoid being overcharged. Newer generic products, compared to older generics, may not have as favorable of a spread, thus the need for MAC.

Collusion between AWP publishers and wholesalers to artificially inflate the AWP, and in turn increase the spread, has led to court cases in the U.S. In these cases, it was alleged that increasing the spread benefited the wholesaler because customers (pharmacies and large institutions) were more likely to buy from them than a competing wholesaler where the spread was not as desirable. The publisher of AWPs profited because pharmacies were more likely to buy the pricing lists from the publisher that noted the higher AWPs used in calculating the spread, than to buy them from other publishers with lower AWPs. Due to this pricing fraud, many payers, including government payers, are no longer using AWP for pricing, and are switching to other more transparent pricing benchmarks, such as WAC or AMP (average manufacturers price). However, AWP may still be found in use in the U.S. because it has been the standard for decades.

However, in order for a pharmacist to access the AWP and to be able to interface with benefits providers, the product associated with an NDC must be in the database. Currently, allergens are on item that does not exist in the database.

SUMMARY

In one embodiment, a method for delivering allergens to a pharmacist in a pre-diluted kit form is provided. The method comprises providing a bulk container of base concentrate antigen containing at least one antigen at a predetermined concentrated level, providing a plurality of sequential bulk containers each containing a fixed amount of a carrier solution for diluting antigens. The method further comprises creating a sequential and more diluted sequence of antigens by the steps of a) dispensing from the bowl container a fixed amount of the base concentrate antigen containing at least one the antigen at the predetermined concentrated level to a first of the sequential bulk containers for being diluted in the carrier contained therein, b) dispensing a fixed amount of the contents of the first of the sequential bulk containers to a next of the sequential bulk containers for being diluted in the carrier contained therein, and c) sequentially repeating step b dispensing a fixed amount of the contents of a previous one of the sequential bulk containers to the next of the sequential bulk containers for being diluted in the carrier contained therein until the last of the sequential bulk containers has contents dispense therein from the previous of the sequential bulk containers. The method further comprises providing a plurality of end-use sealable containers that can receive a finite end amount of diluted antigens, dispensing from each of the sequential bulk containers a finite end amount of diluted antigens into one of the plurality of end-use sealable containers, where in the end-use seal containers filled from each of the sequential bulk containers comprises a group of end-use sealable containers associated with each of the sequential bulk containers, sealing each of the end-use containers after diluted antigens are disposed therein, and disposing a select number of the sealed end-use sealable containers from each of the groups of end-use sealable containers into a container comprising a kit to provide a plurality of kits for dispensing to a patient.

BRIEF DESCRIPTION OF THE DRAWINGS

For a more complete understanding, reference is now made to the following description taken in conjunction with the accompanying Drawings in which:

FIG. 12 illustrates a diagrammatic view of a table in a relational database relating distributed doses back to NDC-bearing dose;

FIG. 12A illustrates a diagrammatic view of a table showing the dilution procedure;

DETAILED DESCRIPTION

Figure 1:
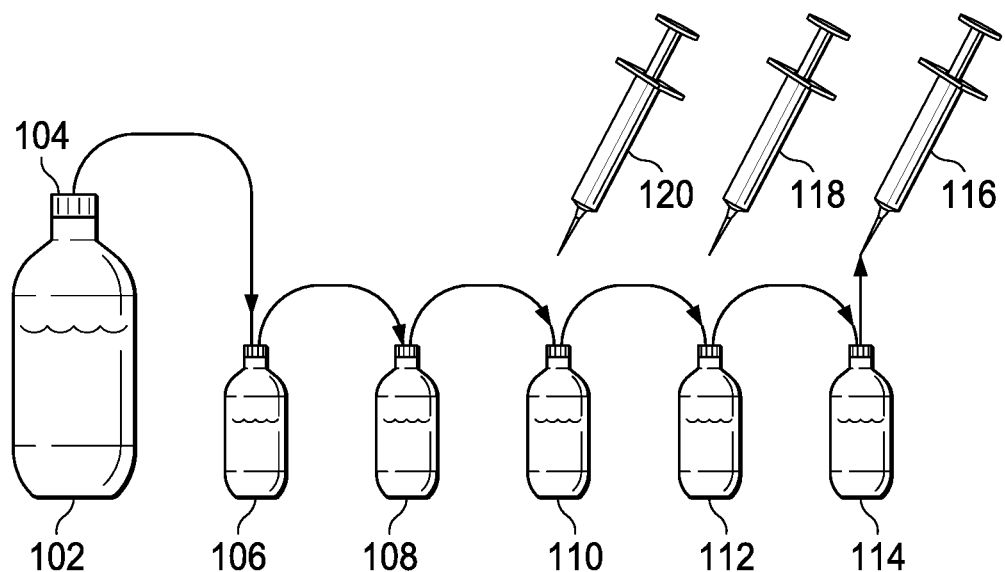
FIG. 1 illustrates a diagrammatic view of a dilution sequence of diluting a concentrated antigen extract.

Referring now to the drawings, wherein like reference numbers are used herein to designate like elements throughout, the various views and embodiments of a method for delivering immunomodulators to a patient for the treatment of allergies in pre-dilution sets are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a depiction of a typical technique for diluting immunomodulators such as antigens, as one example. Preparation of a diluted antigen is performed first by receiving a bottle of extract concentrates from an approved vendor. These are formulated in a given weight/volume (w/v) format with a given antigen associated therewith. For typical antigens such as those associated with the cat antigen, these are relatively well controlled. Typically, a vendor will provide an extract for a single antigen or allergen. Allergens such as pollen and the such are not as well controlled due to the technique for collecting such. In any event, there are typically very few approved vendors for these extracts and allergist typically receives these vendor provided concentrates in a sufficient quantity to make the necessary diluted solution.

Allergen extract is typically comprised of a non-allergenic material, a non-allergenic protein and an allergenic protein. The extraction solutions can be aqueous containing saline and phenol which could be a glycerinated solution. The allergen is added, the units of measure are sometimes referred to as "AU" for "allergy units," typically used for mites. These are referred to as "AU/mL." For such things as grass and cats, the term "BAU" is used for "bioequivalent units." For other allergens, the terminology is, for example, 1:20 w/v, which stands for 1 g source material per 20 mL of fluid. The relationship between BAU and 1:20 w/v depends upon the extract. In any event, there is a defined amount of extract contained within the concentrate.

When concentrated extracts are formulated by an authorized vendor, they are typically provided in standardized versions and non-standardized versions. In standardized versions, they typically are provided in a 50% glycerin dilutant. They can either be a single allergen extract or they can be a mix. For example, one can obtain a "9 Southern Grass Mix (concentrate)" which contains equal parts of: 2 Bermuda at 10,000 BAU/mL, P27 7 Grass at 100,000 BAU/mL, and 15 Johnson at 1:20 w/v. For non-standardized extracts, these are typically provided in either a glycerin dilutant or an aqueous dilutant such as saline. They can be a single extract or a mix. Thus, whenever a concentrated extract is referred to hereinbelow, this refers to a formulation that is provided by an authorized vendor that can be diluted in accordance with the processes described hereinbelow. These are typically provided in the 50 mL bottles with a needle compatible.

Referring back to FIG. 1, the extract concentrate is disposed in a bottle 102. This is a sterile concentrate that has an injection stoppered top 104. There are provided a plurality of five 5 mL sterile injection stoppered bottles 106, 108, 110, 112 and 114, although there could be more and the bottles or containers could be larger than 5 mL. Each of these bottles has disposed therein a defined amount of dilutant, depending upon what the final dilutant is required to be. Typically, the amount of dilutant is 4.5 mL. The procedure is to, first, extract a defined amount of the concentrated extract from the bottle 102 and dispose it in the bottle 106. This is facilitated by the sterile hypodermic that is inserted through the stopper at the top of the bottle 102 to extract concentrate and then the hypodermic is inserted to the stopper in the bottle 106 to inject extract from bottle 102 into bottle 106. Typically, the concentration in the concentrated extract bottle 102 is 1:20 w/v. This will result in a dilution of 1:10 in bottle 106. If the amount injected is 0.45 mL. Then, 0.45 mL of the diluted solution from bottle 106 is extracted and inserted into bottle 108, resulting in a 1:100 dilution of the original concentrate in model 108. The process is repeated up to the bottle 114 to provide a solution that is at a dilution of 1:100,000 of the original concentrate. This is a conventional way to provide a selected dilution of the original antigen. However, it should be understood that any concentration level can be provided from one bottle to the next. Purpose of using the sequential bottles is to allow an achievable portion of one bottle to be distributed to the next bottle, rather than trying to extract a very small amount of the initial concentrated extract. Typically, an allergist will then extract from the desired dilution an amount of the diluted antigen for injection percutaneously. Typically, desensitization is achieved by using the most diluted antigen level initially and sequentially moving up to a higher concentration level over time 1.

Illustrated in FIG. 1 are three hypodermic needles, one selecting a "dose" from bottle 114, and labeled hypodermic 116, a second hypodermic needle 118 for retrieving a dose from bottle 112, a third hypodermic needle 120 for extracting a dose from bottle 110. Each of the hypodermic needles 116, 118 and 120 will contain a different diluted dose. These would typically be separate needles in the event that the allergist or medical professional is injecting a patient. For other purposes, they could be the same needle, depending upon the dose or concentration required. A "dose" is defined by the amount of all the diluted product that would be required for the desired immunotherapy. This is defined by the medical professional. If, for example, bottle 112 were utilized, it may be that 1 mL of diluted solution constituted a "dose." It could be that less than 1 mL constituted a "dose."

In general, the typical distribution chain requires that the allergist or other medical professional purchase the base concentrate and then perform the dilution process. However, this procedure typically requires breaking the seal on the base concentrate bottle and then inserting a needle into the base concentrate bottle for the first dilution step. This occurs multiple times. Thus, multiple needles, each being sterile, can be used one time or, more commonly, a single needle is utilized in association with the base concentrate bottle, with the assumption that, since it does not involve insertion into human flesh, it is still sterile. In any event, this needle must penetrate the rubber stopper seal on the base concentrate bottles multiple times. In fact, these bottles could typically be held upside down and they would leak and, once the seal is broken, there is no sterile cover over the rubber stopper. This is a result of the multiple needle piercings of the rubber stopper. This is also the case with the small 5 mL bottles in that each has to be penetrated at least twice in the higher concentrate bottles. Thus, the last bottle that the allergist has would be a 5 mL bottle and this bottle would already have one piercing of the rubber stopper seal in order to provide the initial dilution level into the carrier material, such as saline. Thereafter, a patient might be able to receive 5 or 10 doses from that particular bottle, requiring 5 or 10 more piercings of the rubber stopper. During this time, of course, there is no seal over the rubber stopper.

Figure 2:
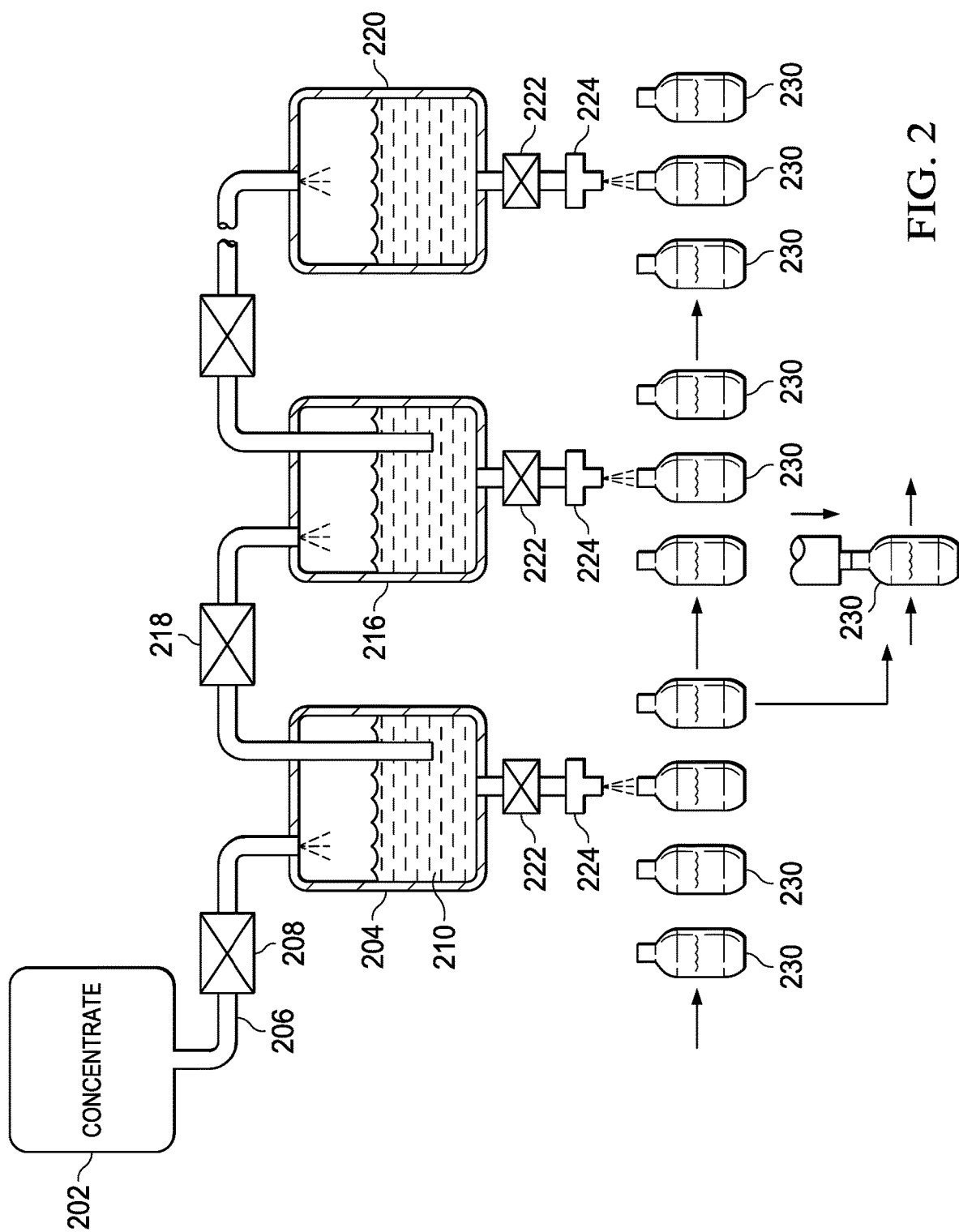
FIG. 2 illustrates a diagrammatic view of a production line for filling distribution bottles.
Figure 3:
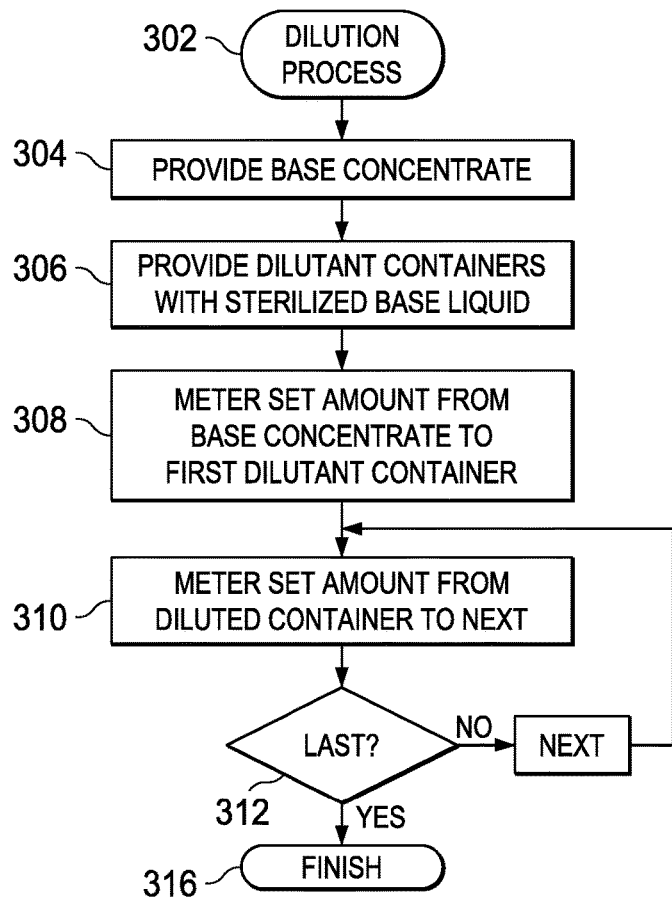
FIG. 3 illustrates a flow chart for the dilution process.
Figure 4:
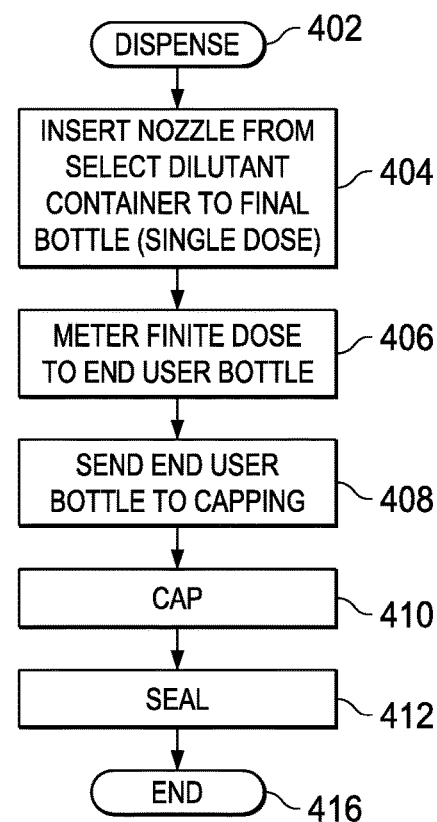
FIG. 4 illustrates a flow chart for the dispensing process.

In order to solve this problem, a process is provided whereby the concentrate bottles are produced from a sterile environment container which Artie has the dilutant provided thereto. This is illustrated in FIG. 2. In this embodiment, a large bottle of base concentrate 202 is provided at a first concentration. This is then metered into a first dilutant reservoir 204 via a tube 206 and a metering valve 208. The first dilutant container 204 has contained therein a carrier liquid 210 which can be, as described herein below, any of a number of materials, such as saline, glycol and the such. Typically, this depends upon the base carrier material associated with the concentrate 202. By knowing the volume of the material to 10 within the reservoir 204 prior to metering therein of the concentrate 202 with the metering valve 208, a very accurate amount of concentrate 202 can be dispensed within the reservoir 204. This metering valve 208 can be controlled to such a level that a very fine and controlled concentrated level can be defined. At this point in the process, the concentrate 202 defines a "batch" material that, for some allergens, is important. For example, if the allergen was related to pollen or the such, this can vary depending upon the year, the production harvest, the quality of harvest, etc. By defining a batch, and controlling the quality and the concentration level at each step in the dilution level, a very controlled dilution level can be provided for that particular batch.

Figure 5:
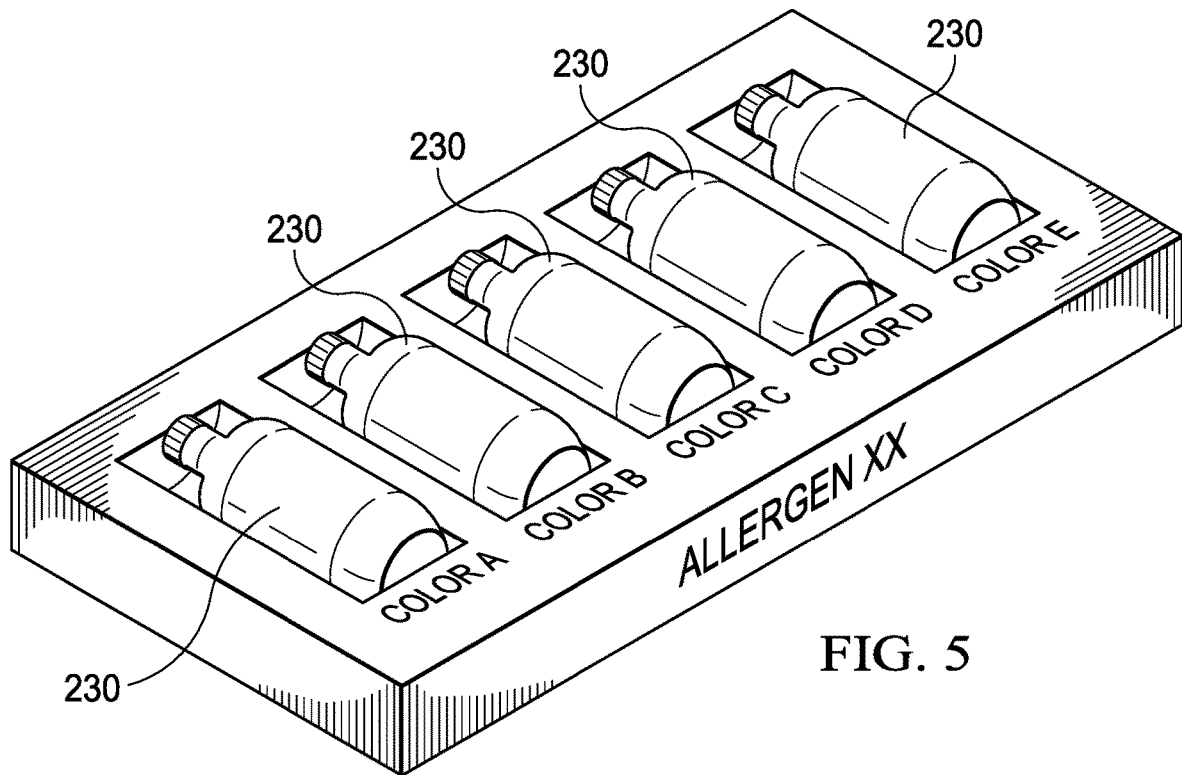
FIG. 5 illustrates a diagrammatic view of a color-coded box with different diluted levels of allergens.

Once the concentrated level or dilution level in the bottle has been defined, this is then utilized to provide a controlled amount of diluted allergen to a second dilution bottle 216 through a metering valve 218. This is repeated for multiple bottles down the line to a last bottle 220. Thus, there are then provided a plurality of larger vessels with controlled dilution levels at each diluted stage in a sterile environment. Each of these bottles 204, 216 and 220 has associated therewith a control metering valve 222 and a dispensing nozzle 224 that is operable to dispense diluted allergen material into a receptacle. This metering valve 222 and associated nozzle 224 are all approved to interface with an approved bottle.

In the dispensing process, there are provided for each dilution stage a plurality of bottles 230. Each of these bottles has a shape and opening that is approved to be interfaced with the nozzle. Each is passed by the nozzle and an exact amount of diluted material, the allergen, dispense therein. Thereafter, each bottle 230 is then subjected to a Procedure which inserts the rubber stopper and the seal there over. The result is a bottle with a defined dosage amount at a defined concentration level for a known batch of allergen, all of which is a sterile environment. The allergist or medical professional need only then remove this seal, insert the needle through the rubber stopper and extract the appropriate amount of diluted allergen. This particular bottle 230 is designed to be a single dose. Thus, the actual amount of material disposed within the bottle will be approximately 1 mL. Typically, the bottles are 5 mL bottles. In this situation, that 5 mL bottle can be modified to maintain the same size but only provide for a single 1 mL dose. This will be described hereinbelow.

Referring now to FIG. 3, there is illustrated a flowchart for the overall dilution process, which is initiated at a block 302. The process flows to a block 304 to provide the base concentrate. As noted hereinabove, the base concentrate is typically associated with a fixed batch so that it is a well-controlled product and this is a sterile bottle within a sterile environment and the size can be larger than typically distributed to an allergist. The process flows to a block 306 wherein the various dilutant containers are provided with a sterilized base liquid such a saline or glycol, depending upon intended final use. The process then flows to block 308 wherein a metered amount of dilutant is passed from the base concentrate vessel to the first dilutant container. The process then flows to a block 310 wherein a metered amount of diluted allergen is transferred from the previous bottle to the next bottle until the last bottle is complete, which is determined at a decision block 312. This will then result in multiple vessels of diluted allergen at the appropriate diluted level for final dispensing. The program then flows to a block 316.

Referring now to FIG. 4, there is illustrated a flowchart for the dispensing operation, which is initiated at a block 402. The process flows to a block 404 wherein a nozzle is inserted from the select dilutant container or vessel to the final dispensing bottle, typically a single dose bottle. The process then flows to a block 406 to meter a finite dose to the end user bottle. Again, this could be a 1 mL dose in a 5 mL bottle or a 1 mL dose in a 1 mL bottle. The process then flows to a block 408 to send the end user bottle to capping, followed by a process block 410 to dispose a cap on the bottle, this being a rubber seal to allow insertion of the needle there through, and then to a seal block 412 to provide a sterile seal over the bottle and then to a terminate block 416.

Referring now to FIG. 5, there is illustrated a depiction of a delivery container for the final allergen in the bottles 230. The bottles would typically be controlled such that they would have, for example, a very distinctive color associated with each diluted level. The highest concentration bottle would be a bottle that would have to be carefully dispensed to a patient, as, if not adequately desensitized to the allergen, this could result in anaphylactic shock to the patient. Thus, it is important that the correct dose at the correct dilution level is administered at a particular time. This color coding process for any type of identification process clearly presents to the medical professional some clear indication of the concentrated level of allergen. Typically, these allergens will be provided in a kit form. For example, it may be that a patient would require the lowest concentrate level of the allergen three times per week for two weeks, followed by the next concentrated level of allergen two times per week for one week, etc. Thus, the various diluted levels of concentrate would be provided in single-dose bottles to, for example, a pharmacy, which would dispense the particular dosages. The first thing is that they would be from a common batch and they would be provided to the patient in the appropriate presentation. For example, the patient might receive a first box of six bottles 230 at the lowest concentrate level for the first two weeks. The pharmacist then would provide the second part of the prescription for the second level in the form of two bottles of concentrate at the next level, this all being color-coded. The box might be color-coded, as well as the bottles. Again, each of these bottles would be a single dose. Since they are all single-dose and contained within sterile bottles, the shelf life is considerably longer.

Figure 6:
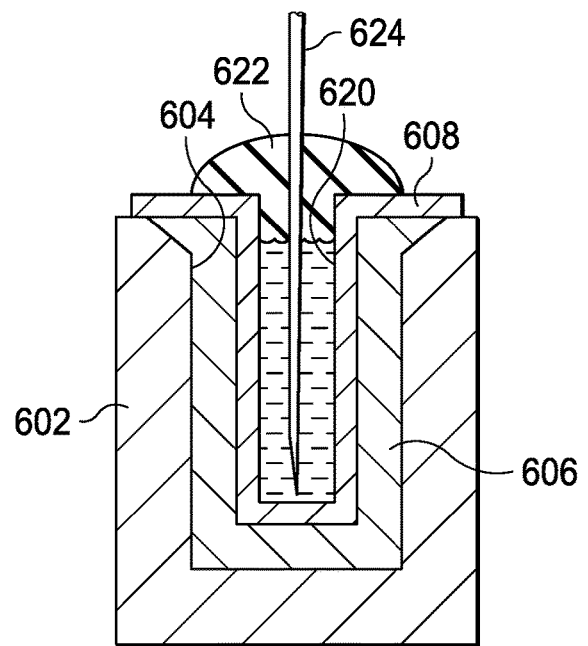
FIG. 6 illustrates a cross-sectional view of a low dose bottle.

Referring now to FIG. 6, there is illustrated a cross-section of a typical bottle that would be involved with respect to providing a single dose of 1 mL in a larger standard 5 mL bottle. A 5 mL bottle is represented by a bottle 602. This bottle 602 has an opening 604 that is provided for the 5 mL bottle. An insert 606 is provided for filling space within the bottle. This can be any type of plastic insert, etc. A smaller insert bottle 608 is disposed within the insert 606 to provide an elongated interior 620 which has a volume slightly in excess of 1 mL, such that a 1 mL dose can be disposed therein. This elongated interior is covered with a rubber stopper 622 such that a needle 624 can be disposed there through and be able to extract 1 mL of diluted antigen. If not for the elongated opening 620 facilitated by the insert 606 in the bottle 608, the 1 mL of diluted antigen would be disposed at a lower level and would be more difficult to extract.

Figure 7:
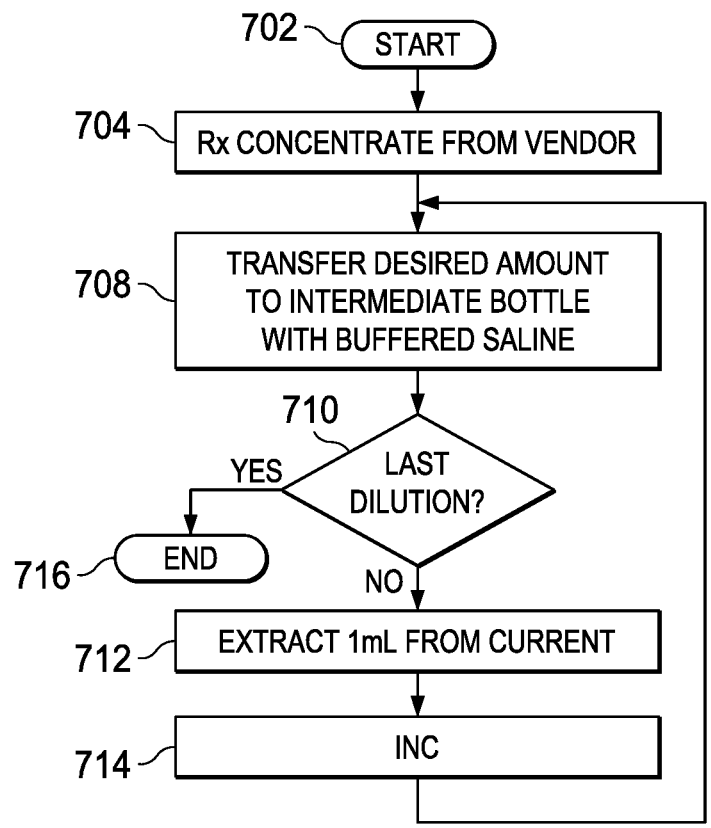
FIG. 7 illustrates a process flow for diluting an antigen extract.

Referring now to FIG. 7, there is illustrated a process flow for the embodiment of FIG. 1. This is initiated at a process block 702 and then proceeds to block 704 wherein a certain amount of concentrated extract is received from a vendor, this being a qualified or authorized vendor for the extract. This is typically at a predetermined concentrate level of, for example, 1:20 m/v. The process then flows to a block 708 wherein a defined quantity of, for example, 0.45 mL is transferred to a 5 mL bottle which already has a quantity of 4.5 mL buffered saline solution disposed therein. The process then flows to a block 710 to determine if this was the last dilution step needed, as described hereinabove, depending upon what level of dilution is necessary. If, for example, by steps of dilution are required for a particular patient, and all five steps would be processed. However, it is not necessary to do all five steps if an intermediate dilution is required. This essentially customizes the overall operation for a particular patient. Further, the industry is so regulated such that only 5 mL bottles can be utilized for this dilution process. Thus, it will only be a maximum of 5 mL of diluted material available at any step prior to proceeding to the next step. Thus, if all 5 mL are required, then the next step is not desired or useful. If it is not the last dilution step, the process flows to a block 712 to extract 0.45 mL of diluted antigen from the current 5 mL bottle and then flows back to the input of the process block 708 after incrementing the bottle count at a block 714. This continues until the last dilution, at which time the process flows from the block 710 to a terminate block 716. Again, any type of carrier could be utilized and bottles larger than 5 mL could in fact be utilized. This all depends upon the number of "doses" at a particular diluted level that are required by the physician right the initial script or prescription.

Figure 8:
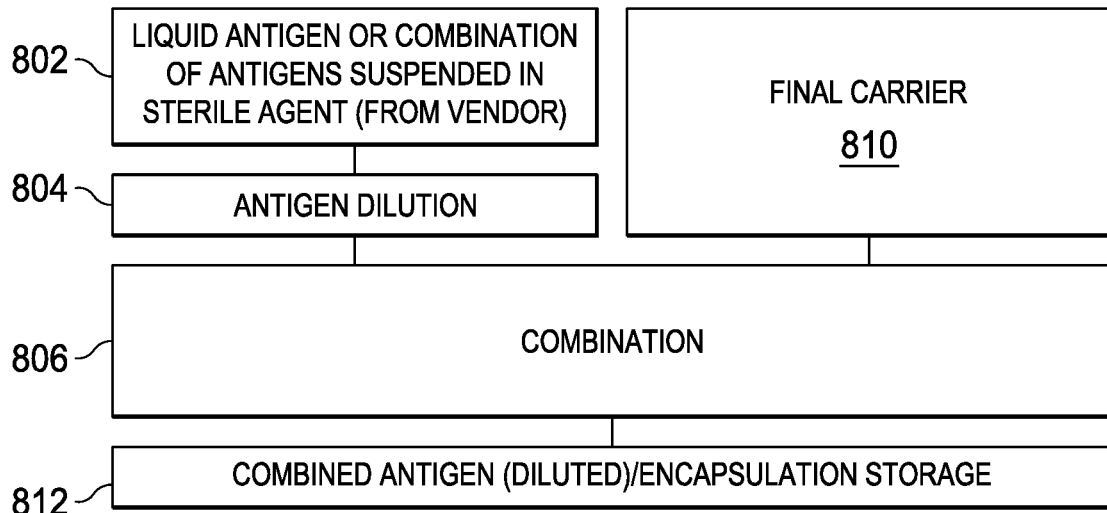
FIG. 8 illustrates a process flow for the overall distribution chain.

Referring now to FIG. 8, there is illustrated in overall flow of the operation of moving concentrated antigen from a vendor to an end user via a pharmacist. As noted hereinabove, the liquid antigen in a concentrated extract at the base concentrate level that has associated there with an NDC was first received from a vendor that assigned that NDC, which is basically a combination of a single antigen or antigens suspended in a sterile agent. This is indicated by a block 802. The antigen is then diluted by the pharmacist from this extract to a desired diluted level, as indicated by a process block 804. This is combined in a block 806 with a sterile carrier and containment material, i.e., sterile saline solution or, even a transdermal cream, for distribution to a patient. This, as described hereinabove, will typically be a defined number of doses of a single diluted antigen or multiple diluted antigens, wherein a dose is again defined as being a typical dose that a medical professional would administer to a patient in an office visit necessary to achieve a therapeutic result for which a patient could administer to themselves. This is either transferred as a combined antigen (diluted)/encapsulation product for storage on a shelf, as indicated by a block 812, or it would be transferred to a medical professional for a patient for management and disposition.

Figure 9:
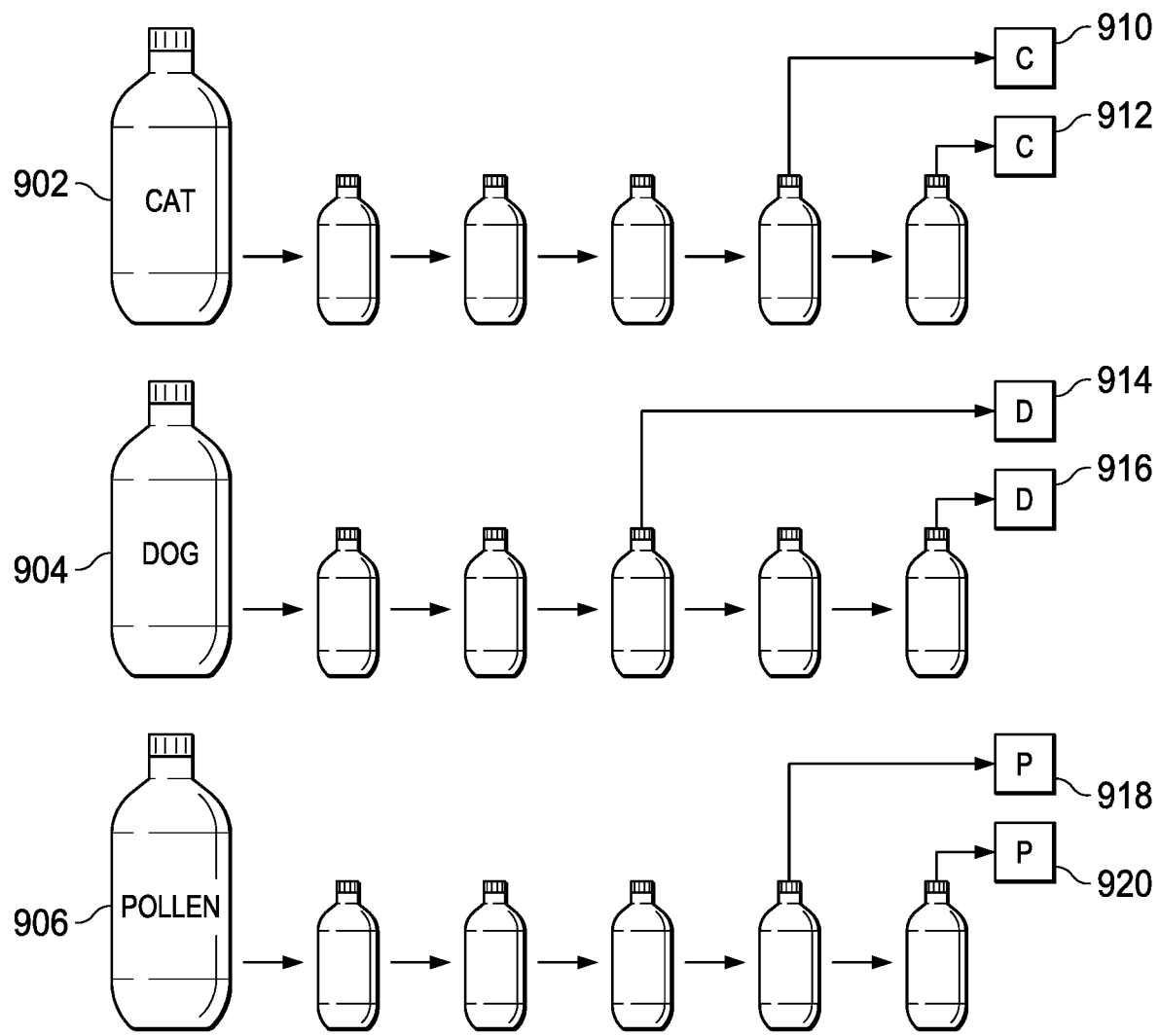
FIG. 9 illustrates a process flow for multiple extracts.

Referring now to FIG. 9, there is illustrated a diagrammatic view of three different extracts of antigens/allergens 902, 904 and 906. Each of these is for a particular antigen or allergen. The first two are for antigens respectively associated with a cat and a dog. The third is for an allergen associated with pollen. They are each diluted in accordance with the process described hereinabove with respect to FIG. 1. As illustrated, the antigen extract in bottle 902 is transferred as a diluted level to either an encapsulation material in a container 910 or 912, each at a different diluted level. This is similarly the case with respect to the antigen in bottle 904 and the allergen in 906 wherein the diluted level of the antigen in the bottle 904 is disposed in containers 914 and 916 and the diluted level of the allergen in bottle 906 is disposed in containers 918 and 920. Typically, any extract will be 100% pure with respect to the particular extract. These concentrated extracts are not typically mixed, which is typically a function that the medical professional or compounding pharmacist will perform. This, of course, is a customized mixture for a particular patient, i.e., this is a patient-specific combination as defined by the medical professional in the script provided to the pharmacist. For storage on the shelf, the operation of FIG. 9 will be facilitated in order to ensure that the containers 910-920 contained only a single antigen. Thus, when transferring the container to a store, for example, this would be stored on the shelf as a single allergen combination of the base concentrate level. The antigens/allergens 902, 904, and 906 may also have been part of the kit described with respect to FIG. 5. In that case, the pharmacist would still create a customized mix for the patient. For example, if the pharmacist received a kit for cat, dog, and pollen, and a prescription for a particular dosage of each (1 mL for example), the pharmacist would create a new bottle filled with one dose of antigen/allergen for cat, one dose for dog, and one dose for pollen. The dosage level (1 mL) may then be tracked back to the NDC code for each antigen/allergen. For example, if 1 mL of cat is associated with an NDC code having a price of $50 associated therewith, and the same is true for dog and pollen, then a total cost of $150 may be appropriate, allowing for the pharmacist to be reimbursed for that amount.

Figure 10:
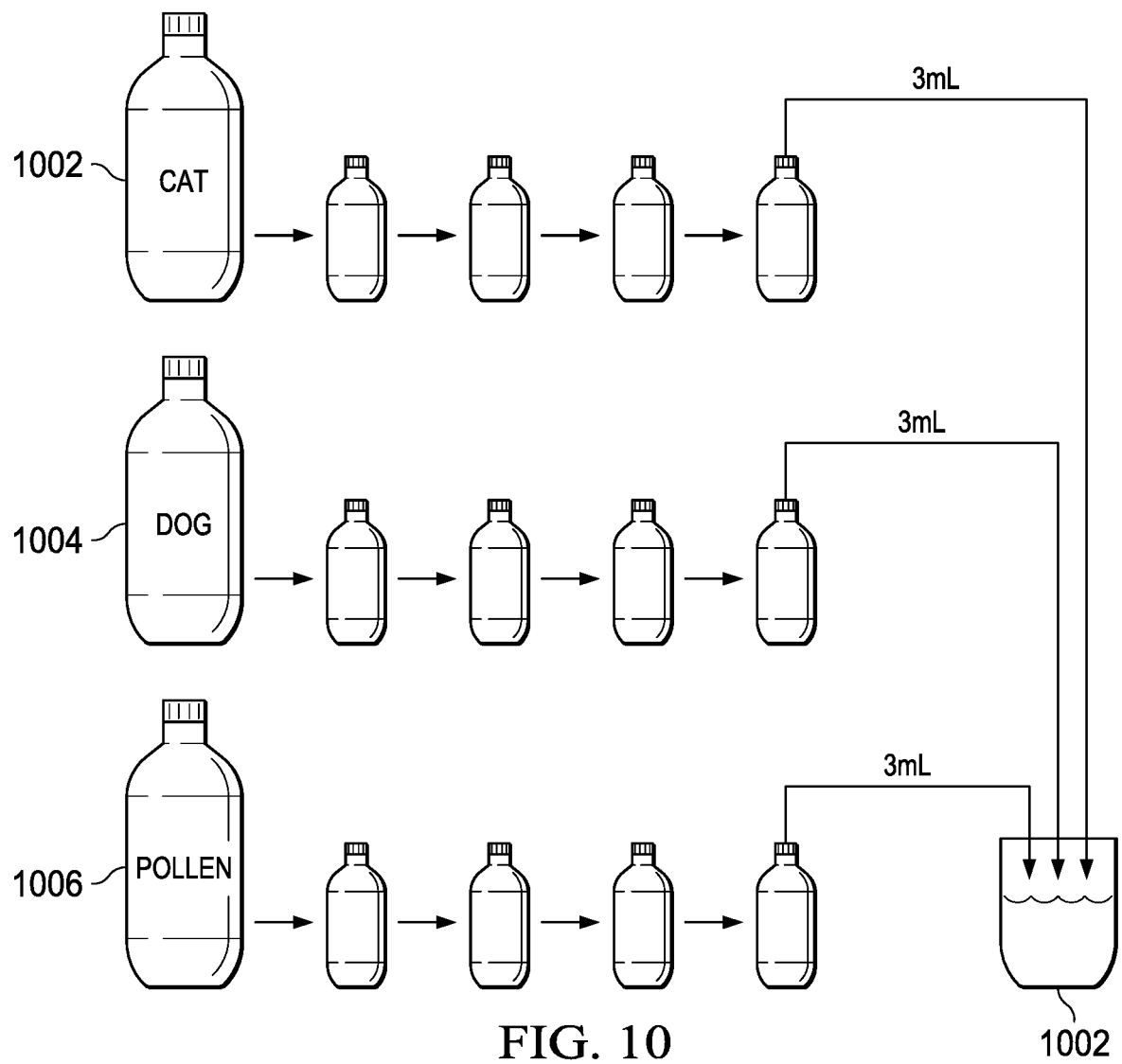
FIG. 10 illustrates an alternate embodiment of FIG. 9.

Referring now to FIG. 10, there is illustrated an alternate disclosure to that of the embodiment of FIG. 9. In this embodiment, each of the immunomodulators or antigens at the concentrated levels in the bottles 902-906 are diluted in accordance with the process noted hereinabove wherein they are sequentially diluted in the associated 5 mL bottles. However, note that only a maximum of 5 mL can be extracted from a given bottle at the last dilution level. If, in this example, it is desired to distribute a predefined number of doses to a final carrier 1002 having a fixed amount of carrier such as saline disposed therein and each dose will add to that material provide the final overall dosage or, alternatively, a viscous transdermal cream can be utilized that is initiated at an original fixed value in grants such that each dose will be associated with a single gram of that transdermal cream material, and then the amount of diluted antigen must be adjusted such that single dose is contained within 0.3 mL of the material. Thereafter, if 3 mL of antigen is extracted from a given bottle, this constitutes 30 doses such that a single dose will be associated with a single dose of the final encapsulation material. In this example, from each of the last dilution bottles for each of the concentrate bottles 902-904, 3 mL is extracted and inserted within the container 1002 containing prescribed level of carrier material, be that saline solution or a transdermal cream. Thus, for each milliliter of saline solution, for example, or each gram of transdermal cream material, there will be a single dose of the particular antigen associated there with. Thus, the carrier material in the container 1002 now acts as a consolidator of all of the antigens for a cocktail.

Figure 11:
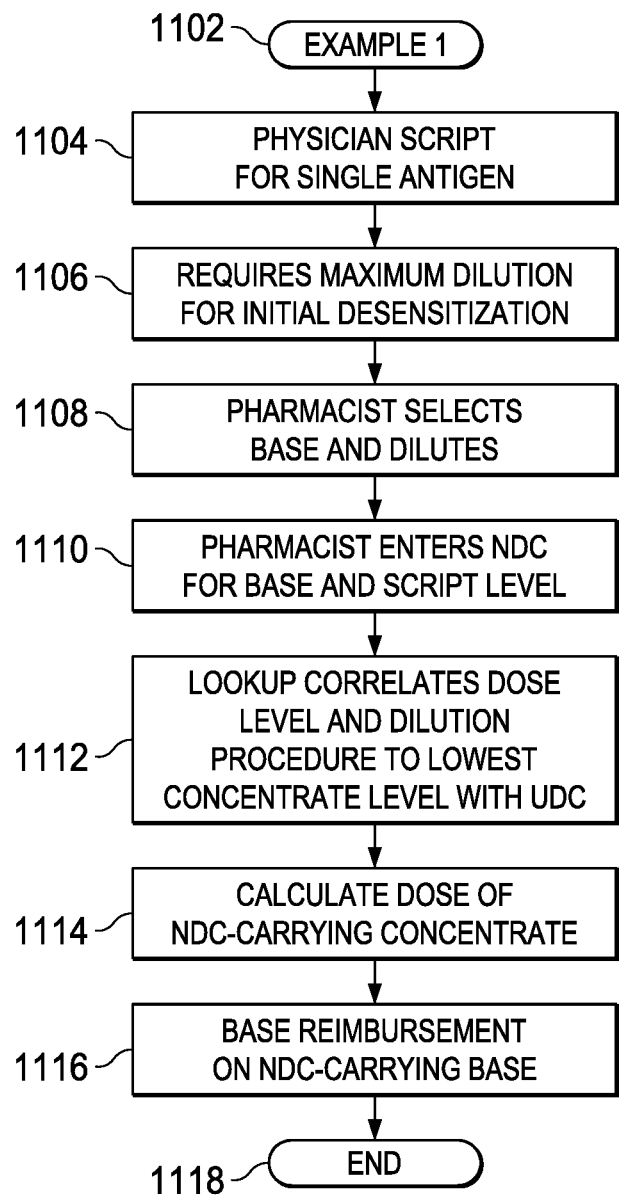
FIG. 11 illustrates a flowchart for one example of processing a physician script.

Referring now to FIG. 11, there is illustrated a flowchart depicting one example of the generation of a script for a single antigen and filling of that fiction based on that script and getting reimbursed therefor. This is initiated at a block 1102 and then proceeds to a block 1104 in order to prepare the physician script for a single antigen. The program then flows to a block 1106 in order to define the requirements of the maximum dilution for the initial desensitization. The physician defined at which level the script is written for. For example, the physician sets forth a regimen. This regimen defines six levels of dilution, each level of dilution are required for a predetermined amount of time. For example, the most diluted level might be required to be administered in three doses per week for three weeks for total of nine doses. The first script would require the pharmacist to deliver to the patient a file containing nine doses at that diluted level of the at least a single antigen. The physician could then require the second higher level to be provided over the course of one week at three doses per week. This might require a second script to be filled by the pharmacist or, alternatively, the pharmacist could fill that script that same time and maintained that particular vial on the shelf for distribution to the patient at a later time, all of this depending upon the script provided by the physician. Of course, the physician could require the patient to come into the office for observation and then write another script. This would be a separate and distinct operation and prescription which would be independently associated with a different set of benefits possibly.

After the dilution level is determined for the initial desensitization or at any level in the desensitization regimen, the program flows to a function block 1108 wherein the pharmacist selects concentrate antigen and then goes to the dilution process required order to achieve the desired diluted level. The program then proceeds to a function block 1110 where in the pharmacist enters the NDC code for the base concentrate level and the script level. Basically, what the pharmacist does is enter the antigen name and the dosage level provided by script. The program then proceeds to a function block 1112 in order to perform a lookup in the PBM database for the particular antigen that is associated with the script. This lookup does a correlation, as will be described hereinbelow, to the lowest concentrate level having an NDC for that particular antigen. Knowing the dilution level and the procedure, it is possible to determine what amount of the NDC-carrying concentrate level for that particular antigen was utilized and then a reimbursement obtained and four. This is indicated by the function block 1114 and 1116. The program then flows to an initial End block 1118.

Referring now to FIG. 12, there is illustrated a table for a single antigen and the overall crosscorrelation information. This is a relational database. In this table can be seen that there is provided a column for the NBC code which is populated for a particular antigen. This indicates the name of the antigen and also information associated there with. There is also a dilution procedure for multiple procedures that can be associated with administering this particular antigen. Since the NBC code associated only with the type of antigen but also the concentration levels, this will be associated with the dilution level to determine what the various dilutant levels are in the overall standard process. As noted, the base level is indicated by a dilutant level D1 or a base concentrate level there than provide five additional dilutant levels D2 through D6. Each one of these dilutant level columns has associated there with a particular range of dilutant levels. As indicated by example, there are levels 1 through 3 for each of diluted levels, with more possible. Therefore, if the most diluted level, D6 were selected and that the procedure required that the dilutant level Z6 for the dilutant level column D6 were selected as the N dilutant level that was required by the physician in the script provided to the pharmacist, this would be what was put into the PBM system. However, there is no NDC associated with this particular antigen at this particular dilutant level. Therefore there must be some crosscorrelation back to column D1 for the base concentrate level, which column has an NDC associated there with. If the final dilutant level was Z6, this could be cross correlated back within the same road to the dilutant level Z1 of the base concentrate. However, although not shown, there could actually be multiple roads associated with the dilutant level Z6, one for each dilution procedure. Thus, the crosscorrelation from the axle in dilutant level back to amount of bass constitute antigen required to process through the diluting procedure requires knowledge of the diluting procedure. This is illustrated in FIG. 12A, wherein each column for the dilutant level Z6 has three has such that there are provided three different amounts of the base extract that would be required, Z1, Z2' and Z". For example, it might be that this requires corresponding levels of 0.8 mL, 1.0 mL or 1.1 mL for those three different levels in order to accommodate the three different dilution procedures S1, S2 and S3. Thus, it is not just a mere crosscorrelation operation but, rather, and overall knowledge of the process that is required in order to determine how much actual product was utilized of the original base NDC-carrying antigen. Only when the amount of the base concentrate NDC-carrying antigen that is utilized is known can the actual dosage be determined. For reimbursement purposes, it is important to know whether 0.8 mL, 1.00 mL or 1.1 mL was use of the base concentrate NDC-carrying antigen is utilized. Reimbursement is calculated based upon this. However, all that is necessary for the pharmacist to do is to put in the end product that was generated and the procedure for coming up with that end product and relate that to the antigen that was utilized.

Figure 13:
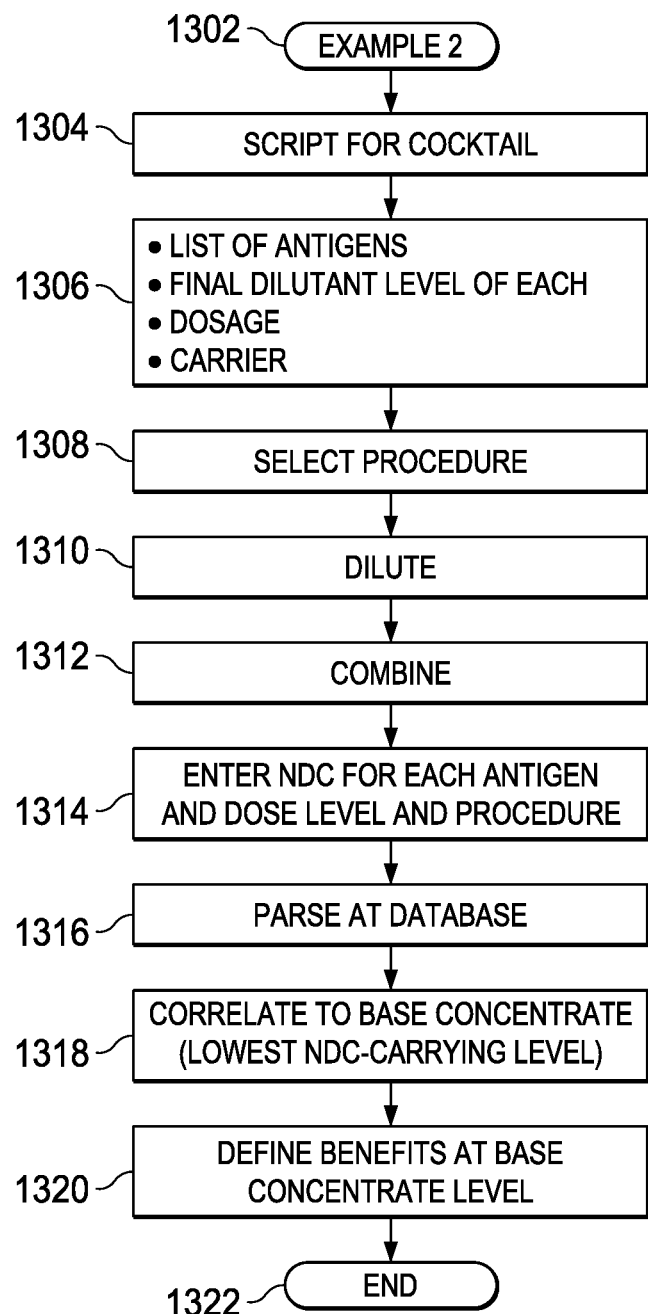
FIG. 13 illustrates a second example of that illustrated in FIG. 11.

Referring now to FIG. 13, there is illustrated a flowchart for a second example for preparing a script for a cocktail, which is similar to the flowchart of FIG. 11. This is initiated at a block 1302 and then proceeds to a block 1304 to generate a script for a cocktail which is a patient-specific cocktail based upon a prick test performed. This is unique to that patient for that particular time. The program then proceeds to a function block 1306 in order to provide in that script a list of the antigens to be placed into the cocktail by the pharmacist, the final dilutant level of each, the dosage and the particular carrier. The program then flows to a function block 1308 in order to select the procedure that the pharmacist will utilize to provide this final diluted product with the prescribed number of dosages. This might be prescribed by the position or it might be selected by the pharmacist. The program then flows to a function block 1310 wherein the pharmacist performs the dilution operation and then combines various antigens into the cocktail, at a block 1312. The program then proceeds to a function block 1314 wherein the NDC for each antigen is entered into PM database, the dose level and the procedure. The program then proceeds to a function block 1316 to parse the particular antigens at the database, this parsing required in order to process each antigen in the database separately, as there must be a crosscorrelation back to each individual antigen, since only each individual antigen has an NDC associated there with. The program then proceeds to a function block 1318 in order to correlate the antigen back to the lowest concentrate NDC-carrying level, as described hereinabove with respect to the embodiment of FIGS. 11 and 12 and then to a function block 1320 in order to define the benefits and then to a function block 1322 in order to end the program, after the cocktail has been distributed to the end user such as the patient or the medical professional.

Figure 14:
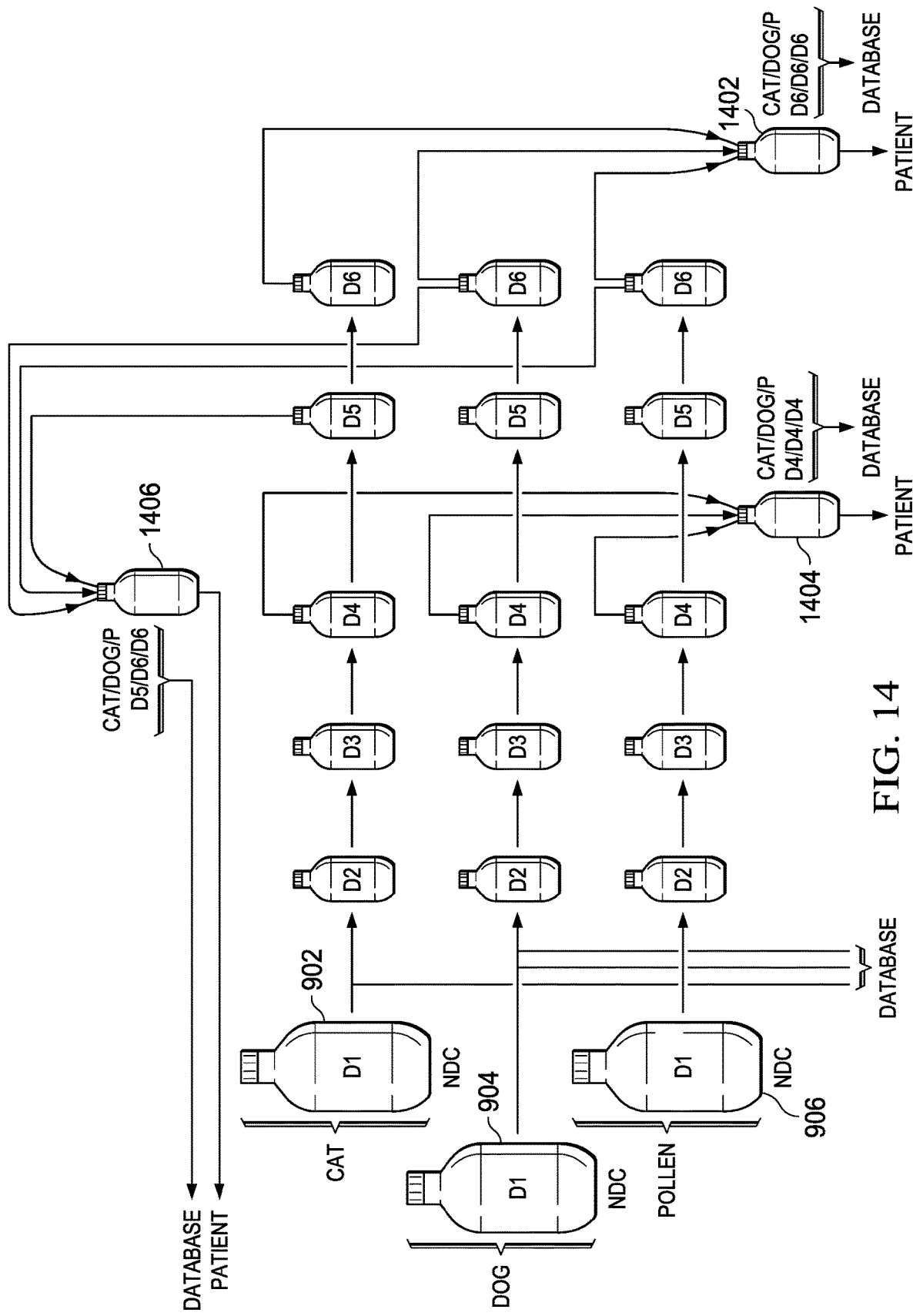
FIG. 14 illustrates a diagrammatic view of processing of a script received from a physician at a pharmacist to compound a patient-specific dosage.

Referring now to FIG. 14, there is illustrated a process, which is similar to that described hereinabove, for creating a cocktail from three different base concentrate antigens 902, 904 and 906, referring hereinabove to the description with respect to FIG. 9. These are diluted down in five separate steps to a final dilution level D6. In a first operation, there is provided a final vial 1402 that receives the final dosage from each of the processes for diluting the initial base concentrate levels. It may be that each of the final vials D6 each have 5 mL contained therein. By containing no carrier material in the final vial 1402, 3 mL of each of the extract can be placed therein resulting in a vial with 9 mL therein. If the physician prescribed the regimen to deliver a 1 mL dose of this concentrated level III times per week for three weeks, this would require nine doses and thus 9 mL of the cocktail. This overall process, for example, would require the pharmacist to understand each step of the dilution process to arrive at the final diluted. Thus, the pharmacist would indicate that there were three antigens in the final vial 1402 and that they were at the concentrate level D6/D6/D6. This would be provided to the PDM database. With this information alone, the system at the PDM database can cross correlate this back to the exact amount of base concentrate level lies for each of three base concentrate antigens 902, 904 and 906 utilized.

Alternatively, there is provided a vial 1404 which is the result of a different selection of cocktails from the D4 level. This, again, would have the re-antigens in the concentrate level D4/D4/D4. This would again pre-provided to the PDM database which would then, based upon the dilutant level for each of the antigens and the procedure utilized to achieve that dilutant level to relate this back to the antigens utilized at the NDC-carrying concentrate level. If, for example, this vial 1404 resulted in 9 mL of material but the physician only required three doses of 1 mL each for two weeks, this would only required 6.0 mL. The pharmacist might only dispense 6 mL out of the 9 mL to the patient or professional. Even though he doses distributed or 6.0 mL, this 6 mL of final product of D4/D4/D4 of Cat/Dog/Pollen antigen has to be related back to the original antigen value.

In an alternate embodiment, there is a vial 1406 provided that has been provided where in it receives diluted antigens from slightly different and vials. In this operation, the three antigens are D5/D6/D6 and this is provided back to the PDM database. Of interest is that all three vials 1402, 1404 and 1406 will each the input to the PDM system with their procedure and the result will be that, for this example specifically, at the reimbursable be the same, as the starting dilutant will be identical. This is procedure specific and script specific, with the cocktail noted as being patient-specific. The antigens/allergens 902, 904, and 906 may also have been part of the kit described with respect to FIG. 5. In that case, the pharmacist would still create a customized mix for the patient. For example, if the pharmacist received a kit for cat, dog, and pollen, and a prescription for a particular dosage of each (1 mL for example), the pharmacist would create a new bottle filled with one dose of antigen/allergen for cat, one dose for dog, and one dose for pollen. The dosage level (1 mL) may then be tracked back to the NDC code for each antigen/allergen. For example, if 1 mL of cat is associated with an NDC code having a price of $50 associated therewith, and the same is true for dog and pollen, then a total cost of $150 may be appropriate, allowing for the pharmacist to be reimbursed for that amount.

Figure 15:
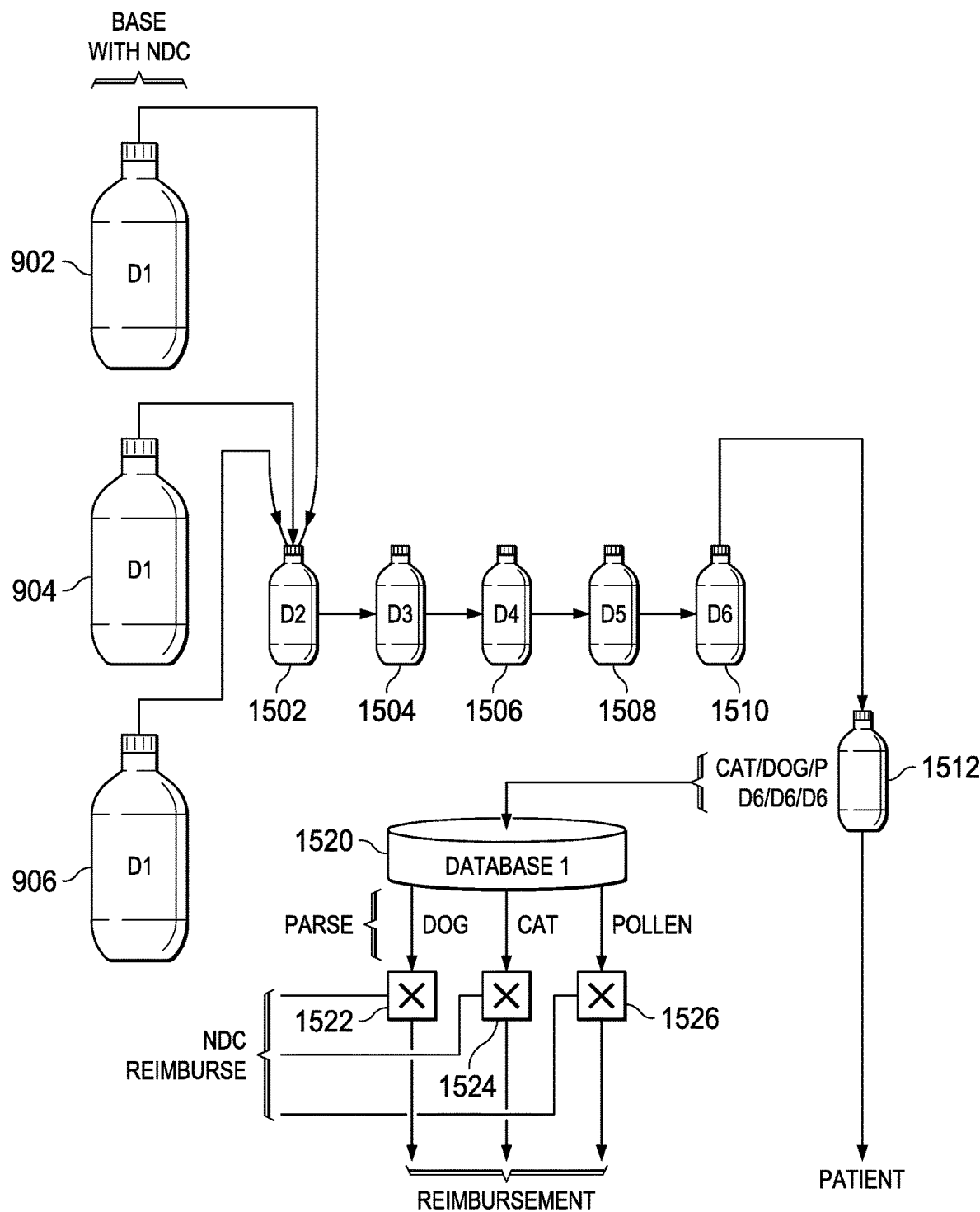
FIG. 15 illustrates an alternate embodiment of that illustrated in FIG. 14.

Referring now to FIG. 15, there is illustrated an alternate embodiment wherein each of the base antigens 902, 904 and 906 are subjected to a different procedure wherein each of the original starting amounts are input to a first diluting vial 1502 and are subsequently diluted through vials 1504, 1506, 1508 and 1510 to a final vial 1512. This is an distributed to the patient. This final vial represents the dilution at the vial 1510, which is D6/D6/D6. This, along with this is procedure is then transferred to the PDM database, as indicated by block 1520, which is then parsed to the specific antigens and into a translator associated with each antigen, indicated by a "X" for the crosscorrelation operation, blocks 1522, 1524 and 1526 associated with the Dog, Cat and Pollen antigens which will then define the reimbursement. Each translation block 1522 will be associated with a reimbursement database for defined benefits associated with the particular antigen. Of course, it is important to know the amount of antigen that was actually utilized in the overall procedure which, again, requires knowledge of the final script dilutant level of the antigen delivered to the patient and procedure for obtaining that diluted level.

Figures 16A, 16B:
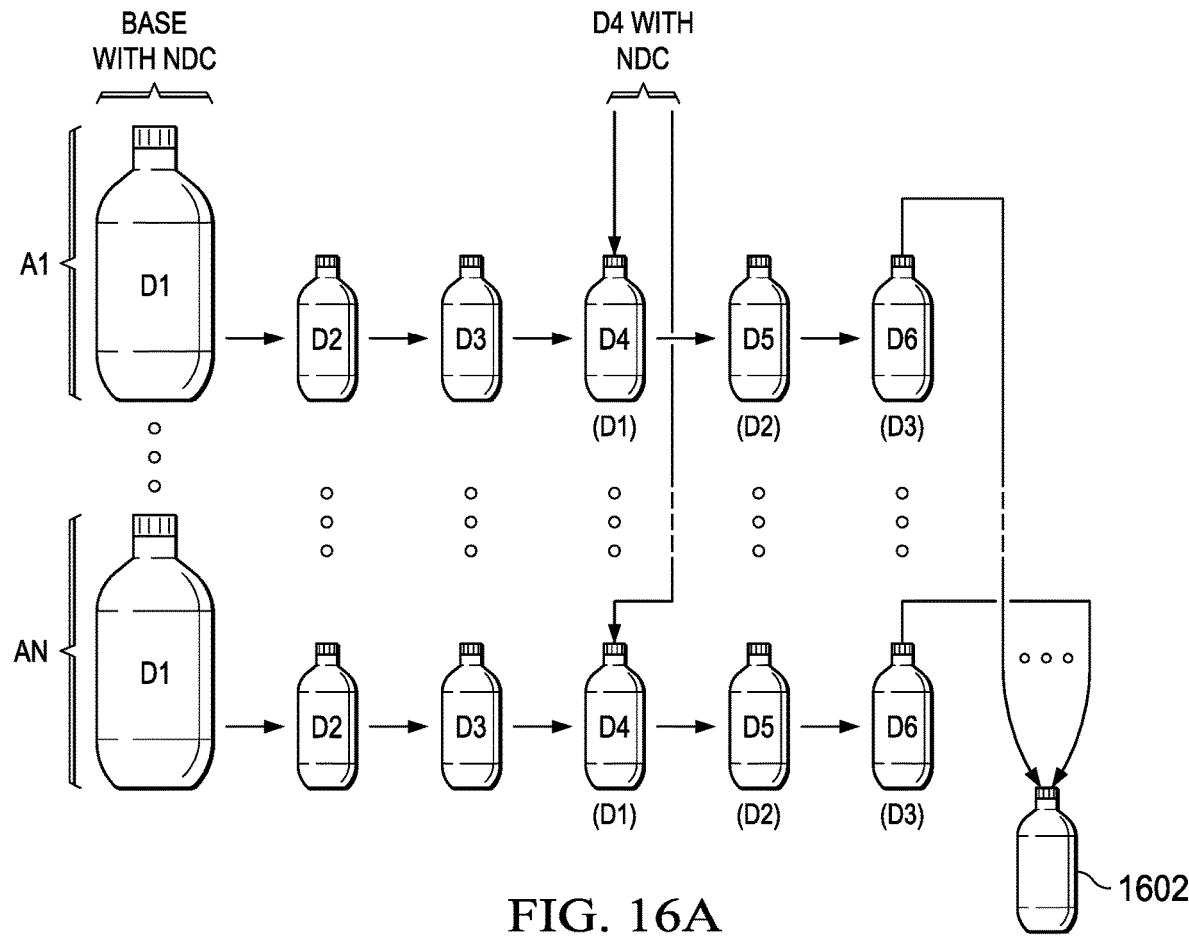
FIG. 16A illustrates a diagrammatic view of a process of filling a script received from a position and FIG. 16B illustrates a table associated with such process.
Figure 17:
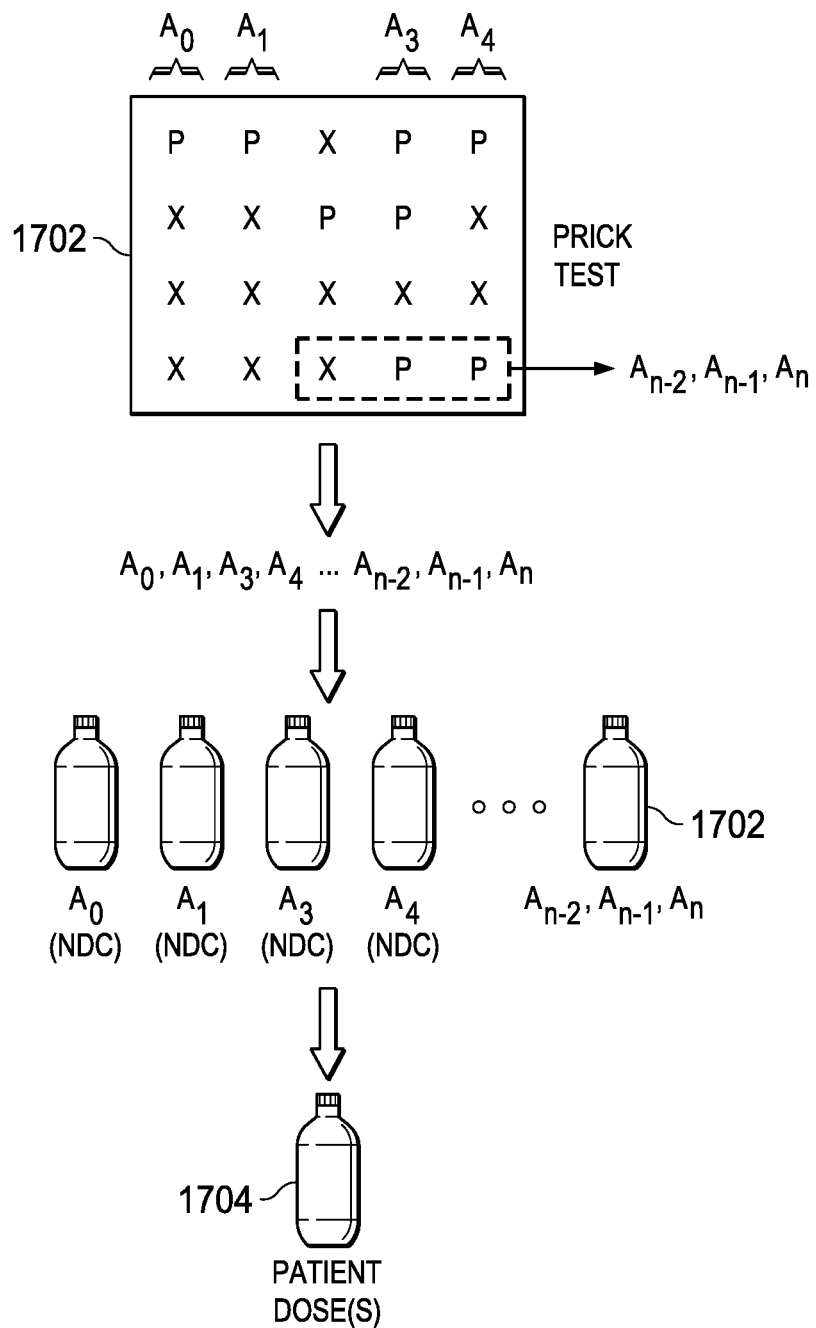
FIG. 17 illustrates an overall process flow illustrating the prick test, the script flowing through to the final patient does.
Figures 18A, 18B:
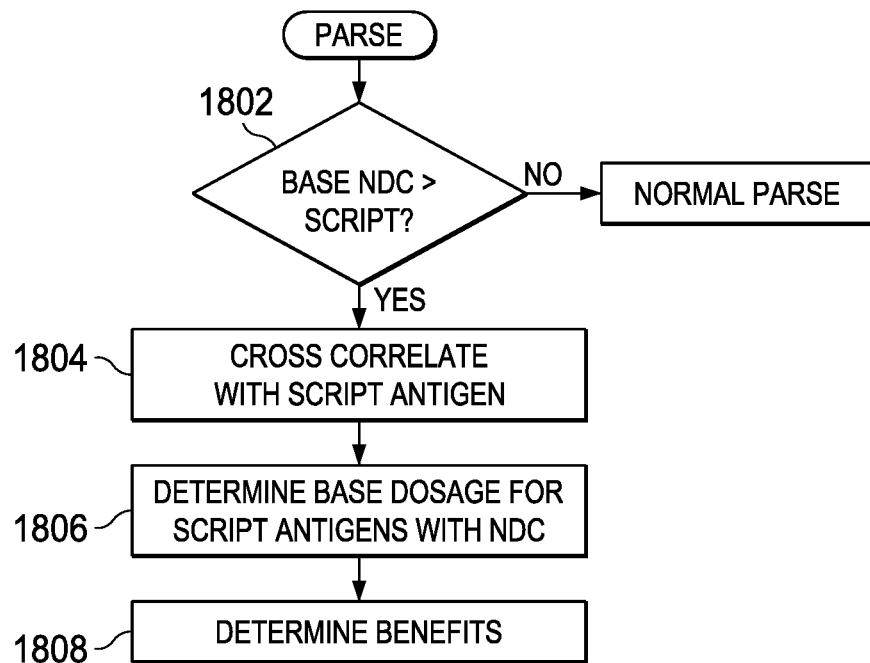
FIG. 18A illustrates a flowchart for parsing an antigen having a base dose with more than the prescribed antigens and FIG. 18B illustrates a table associated with the parsing operation.

Referring now to FIG. 16A, there is illustrated a diagrammatic view of an overall process where in the NDC is associated with an intermediate level of dilutant. In this embodiment, the dilutant level D4 is illustrated as having an NDC associated there with, as well as the base concentrate level of Thus, it is possible that the reimbursement and be defined back to this intermediate concentrate level of. This is indicated in a table in FIG. 16B, wherein the table can have associated with original diluted levels D4, D5 and D6 crosscorrelation relationships with respect to the base concentrate level but, in this table, there are only three diluted levels required, the dilutant level for vial D4, the vial D5 and the vial D6. If the concentrate level at the final vial was X3 based upon the NDC code being at vial D4, all that would be required is to do a crosscorrelation back to the dilutant level required from the file D4. This would be for each of the dilutant set was combined in a vial 1602 from each of the antigens in the script, this indicated as being the antigens A1-N.

Referring now to FIG. 17, there is illustrated a process for mapping prick test to the script. As illustrated, there is provided a diagram of the prick test, indicated by a reference numeral 1702. This diagram 1702 indicates the locations of the particular allergens that were administered to locales on the person of the patient. This diagram illustrates the results with a "P" indicating a positive reaction and that an "X" indicating a negative reaction. Thus, the "P" indicates a sensitivity that must be considered in the script. Of interest is that the particular manufacturers of antigens might have a cocktail already existing in the base concentrate. This is illustrated with the bottom three test associated with antigens A(n−2), A(n−1) and AN. These are the last three antigens in the list. Of these, the last two are positive and the third for the last is negative. However, the script will have to include only the last two for the patient-specific script but the pharmacist only has the cocktail of all three available to them. Thus, the script will have a A0, A1, A3, A4 . . . , A(n−1) and AN as the antigens that are required for the desensitization regimen. This will be provided to the pharmacist which will then select NDC-Kerry antigen bottles A0, A1, A3, A4 . . . , And finally a bottle 1702 containing A(n−2), A(n−1) and AN, wherein only A(n−1) and AN are required in script to fill the prescription. This is then processed to provide the final patient dosage in the cocktail in the vial 1704.

Referring now to FIG. 18A, there is illustrated a flowchart depicting the overall parsing operation before the operation of FIG. 17. In this operation, if the base NDC has a greater number of antigens than the script, a decision block 1802 will determine such and flow to a block 1804. The program will then flow to a function block 1806 in order to determine the basis dosage for the script as required by and set forth by the position of the antigens with the particular NDC, even though that NDC IS associated with more than the antigens required by the script. The program then flows to a function block 1808 in order to determine the benefits. This is illustrated best with respect to the table of FIG. 18B. Here, it is illustrated that there are three procedures for providing the end dilutant level at the vial D6 for each of the antigens in the cocktail antigen vial 1702. If a certain amount of antigen is extracted from this particular vial 1702, it will contain all three antigens. At a particular concentrate level at the level D6, this will yield the necessary concentrated level of the two antigens desired even though the third antigen is included. Since the final dilutant level is known for the two prescribed antigens, they can be cross correlated back to the amount of antigen that was actually extracted. However, for example, if 3 mL of the extract in vial 1702 were extracted, this might represent a particular portion of a 100 mL bottle and, if all three antigens have been prescribed, this would be the basis for the reimbursement. However, if only to antigens were prescribed, only two thirds of that prescribed extract would be reimbursed. Thus, by utilizing known script at the known dilutant level, this can be cross correlated back via the standard procedure (or whatever procedure is utilized) to what was actually utilized of the NDC-carrying base concentrate material to actually derive the final prescribed and delivered antigen to the patient.

Although the preferred embodiment has been described in detail, it should be understood that various changes, substitutions and alterations can be made therein without departing from the spirit and scope of the invention as defined by the appended claims.

What is claimed is:

1. A prediluted kit including a range of prediluted doses of allergens for dispensing to a patient, comprising:

a container having a plurality of receiving pockets, each being associated with one of a plurality of sequential diluted allergen levels all based on a base concentrate antigen wherein the base concentrate antigen includes at least one specific antigen;

a plurality of end-use sealable containers of prediluted antigens, wherein the plurality of end-use sealable containers are sterile, wherein each one of the plurality of end-use sealable containers is at a defined level and disposed in one of the plurality of receiving pockets, wherein each one of the plurality of end-use sealable containers is prepackaged as already including the base concentrate antigen at a sequential dilution level diluted in accordance with a predetermined sequential dilution process to provide sequentially lower dilution levels for use in an allergy desensitization regimen prescribed by a medical professional, and wherein each one of the plurality of end-use sealable containers includes at least one insert operable to:

provide an elongated interior in the end-use sealable container, the elongated interior having a volume corresponding to at least a dose; and fill space within the end-use sealable container to dispose a prediluted antigen at an elevated level in the end-use sealable container for extraction; and an indicator disposed in association with each of the plurality of receiving pockets indicating the dilution level of the associated one of the end-use sealable containers included therein.

2. The kit of claim 1, wherein each of the plurality of end-use sealable containers includes more than one diluted antigen.

3. The kit of claim 1, wherein each of the plurality of end-use sealable containers includes only a single diluted antigen.

4. The kit of claim 1, wherein a National Drug Code (NDC) of the base concentrate antigen is indicated on the container.

5. The kit of claim 1, wherein the indicator comprises a color code, there being a separate color code associated with each dilution level and wherein each of the end-use sealable containers associated with each of the dilution levels has a corresponding color code disposed there on.

6. The kit of claim 1, wherein each of the end-use sealable containers contains only a single dose of diluted allergen, as defined by the medical professional.

7. The kit of claim 2, wherein a plurality of National Drug Codes (NDC) is indicated on the container, wherein each of the plurality of NDCs is associated with a base concentrate antigen of each of the more than one diluted antigen.

* * * * *